United States Patent [19]

McClees et al.

[11] Patent Number: 5,437,623

[45] Date of Patent: Aug. 1, 1995

[54] WOUND DRESSING SECUREMENT SYSTEM

[75] Inventors: Nancy J. McClees, Westerville, Ohio; John L. Blum, South Toms River; Mark F. Lesko, Jackson, both of N.J.

[73] Assignee: E. R. Squibb & Sons, Inc., Princeton, N.J.

[21] Appl. No.: 100,828

[22] Filed: Aug. 2, 1993

[51] Int. Cl.⁶ ............................................. A61F 13/00
[52] U.S. Cl. ...................................... 602/59; 602/53; 602/78; 128/846
[58] Field of Search ................. 602/1, 41, 42, 43, 44, 602/45, 47, 53, 59, 78, 79; 128/896, 887, 889

[56] References Cited

U.S. PATENT DOCUMENTS

| | | | |
|---|---|---|---|
| 3,417,749 | 12/1968 | Bailey | 602/79 |
| 3,888,297 | 6/1975 | Stenvall | 602/59 |
| 4,381,611 | 5/1983 | Wishman | 602/45 X |
| 4,732,146 | 3/1988 | Fasline et al. | 602/79 |
| 4,981,465 | 1/1991 | Ballan et al. | 128/887 X |
| 5,086,763 | 2/1992 | Hathman | 602/79 X |
| 5,230,350 | 7/1993 | Fentress | 128/846 |

FOREIGN PATENT DOCUMENTS

89/11844  12/1989  WIPO ............................... 128/846

*Primary Examiner*—Sam Rimell
*Attorney, Agent, or Firm*—Stuart E. Krieger

[57] ABSTRACT

The wound dressing securement device has one or more flexible adhesive base member strips that are secured to the skin around or at opposite sides of a wound with sufficient clearance for a wound dressing. A plurality of sheet retention members joined to one or more of the base members project vertically from an exposed surface of the base member. A flexible, foldable, stretchable hold-down sheet member has a plurality of openings to engage with engagement heads provided on the sheet retention members. The hold-down sheet member is sized to form a cover for the underlying wound dressing and bears against the wound dressing to hold it in position on the wound. When the wound dressing is to be changed, the hold-down sheet member is disengaged from the sheet retention members to uncover the wound dressing, and make it accessible for removal and replacement. The adhesive base member(s) remain in place during repeated changes of the wound dressing.

19 Claims, 5 Drawing Sheets

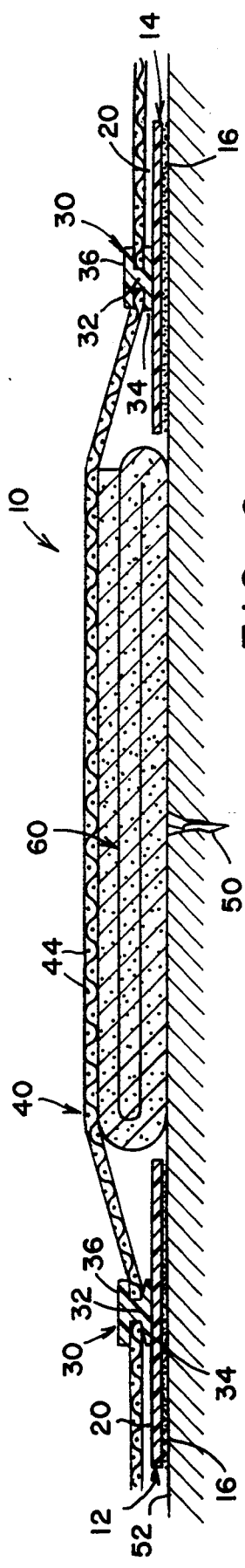
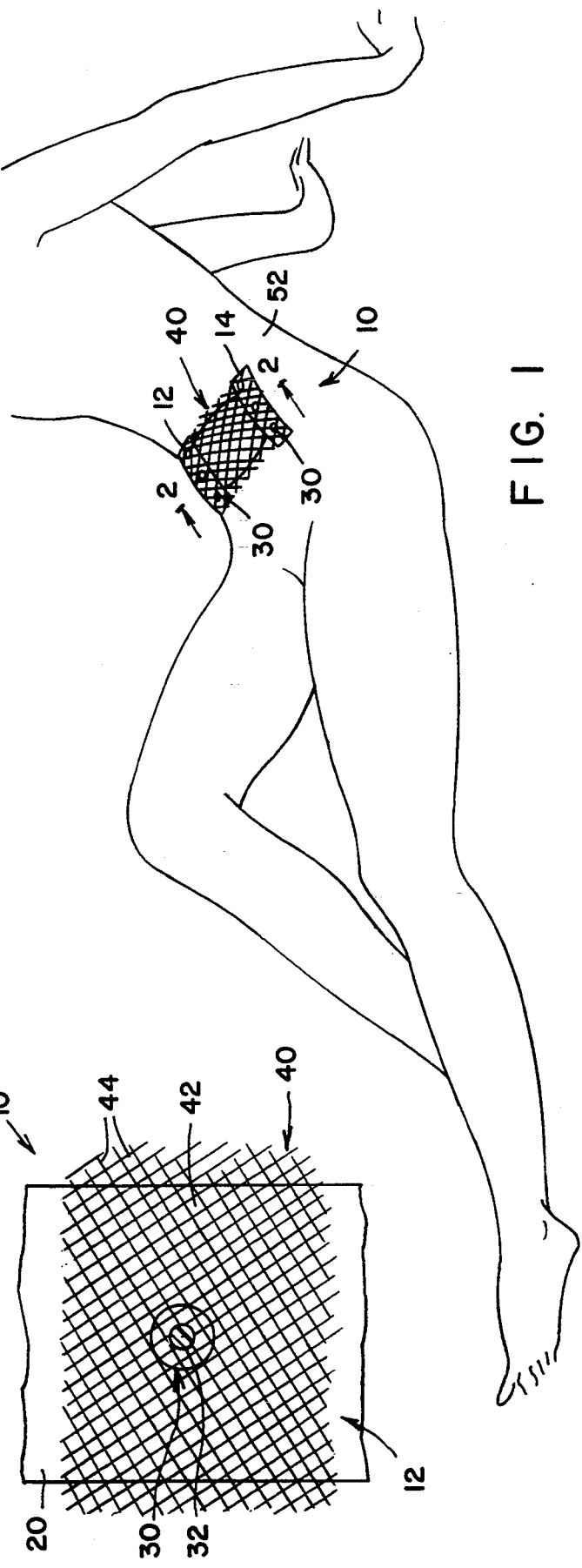
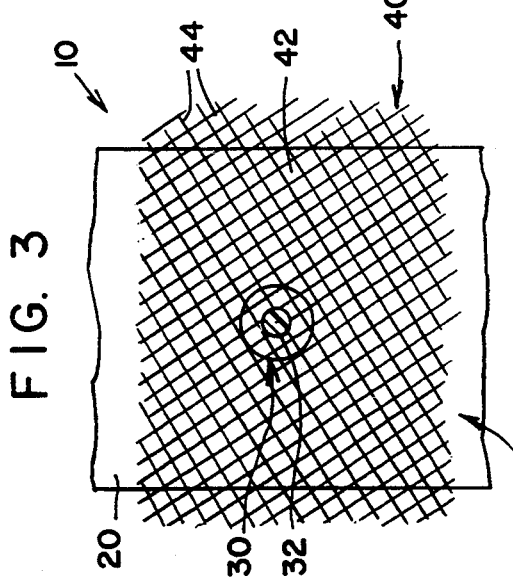

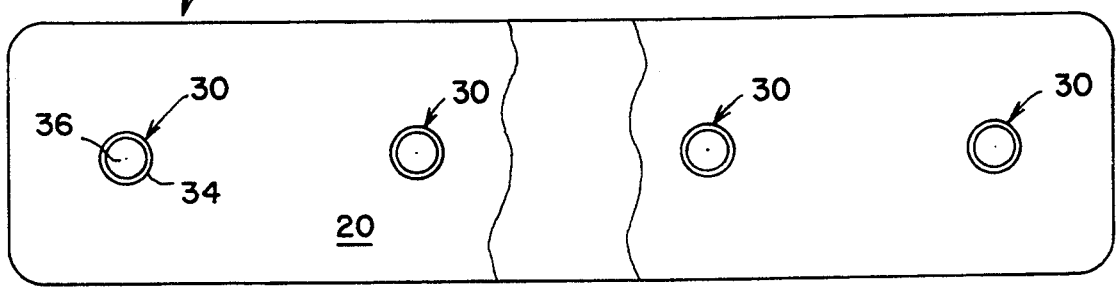
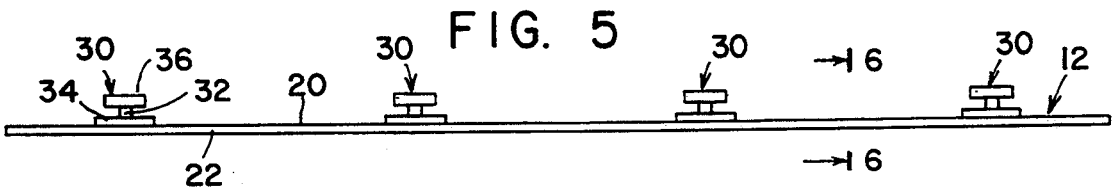
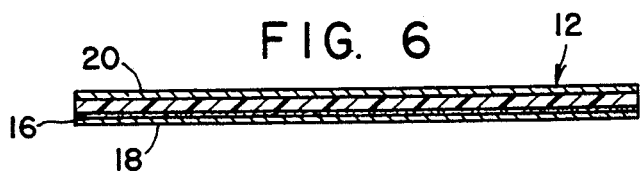
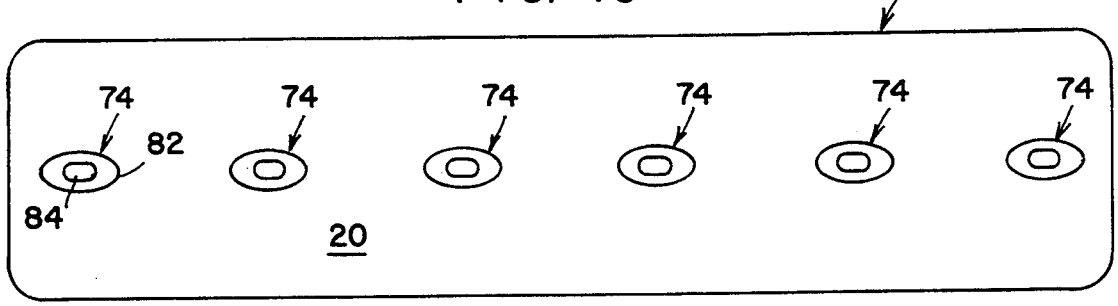
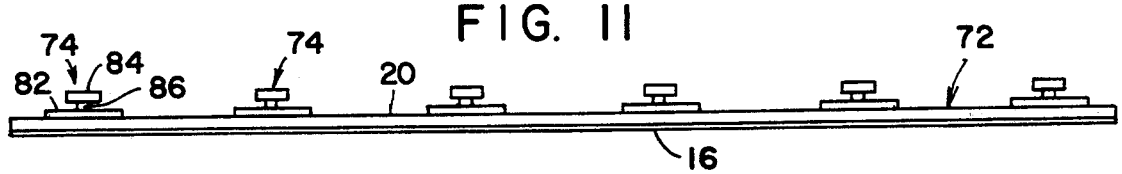
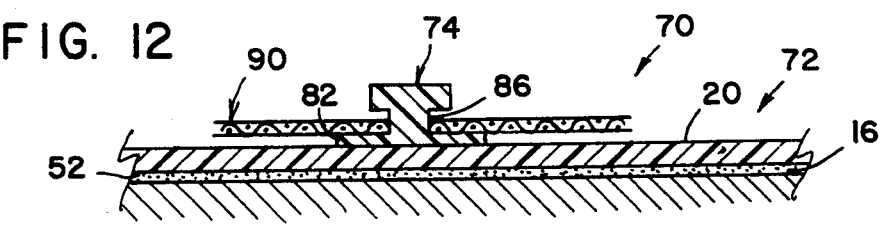

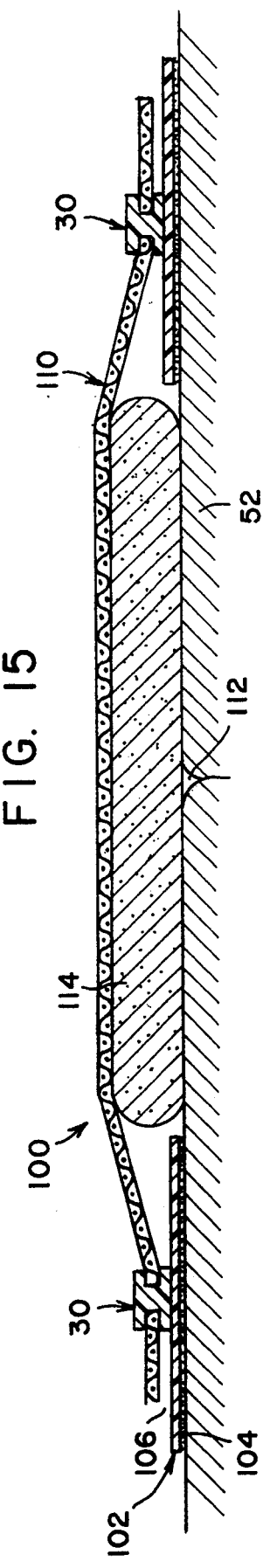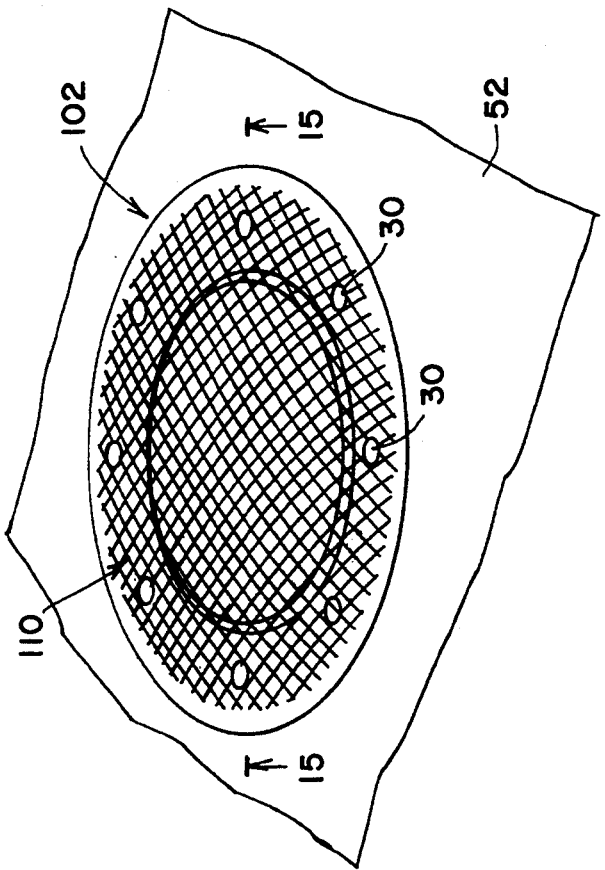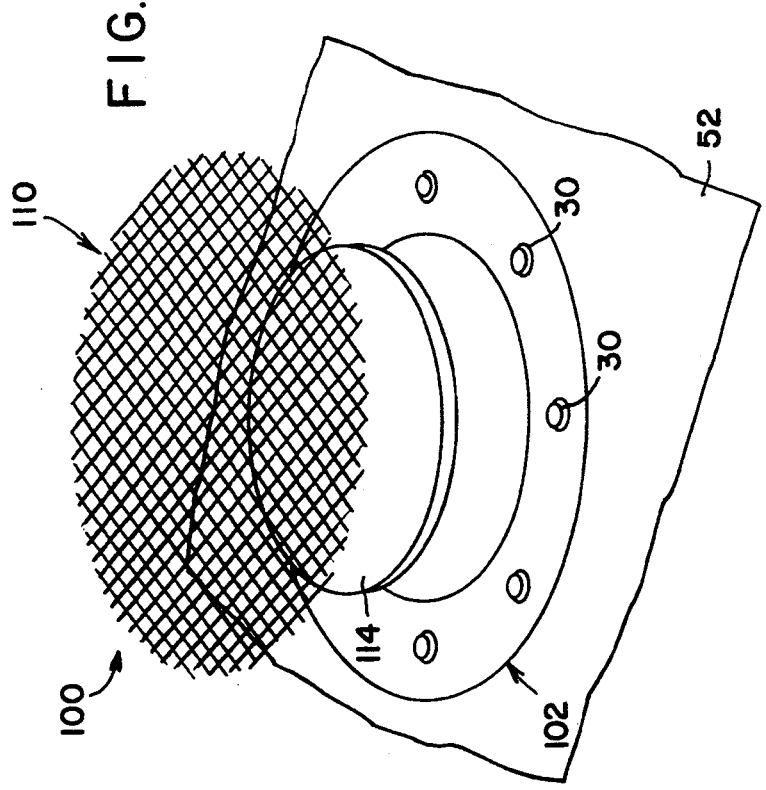

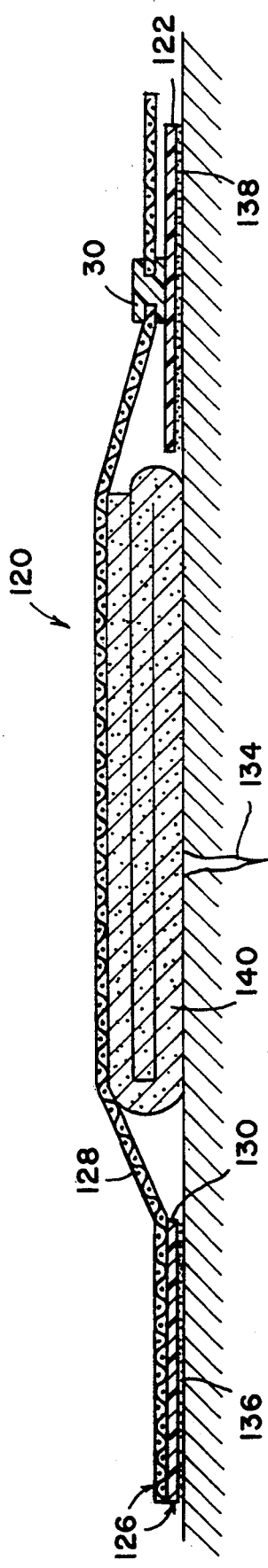
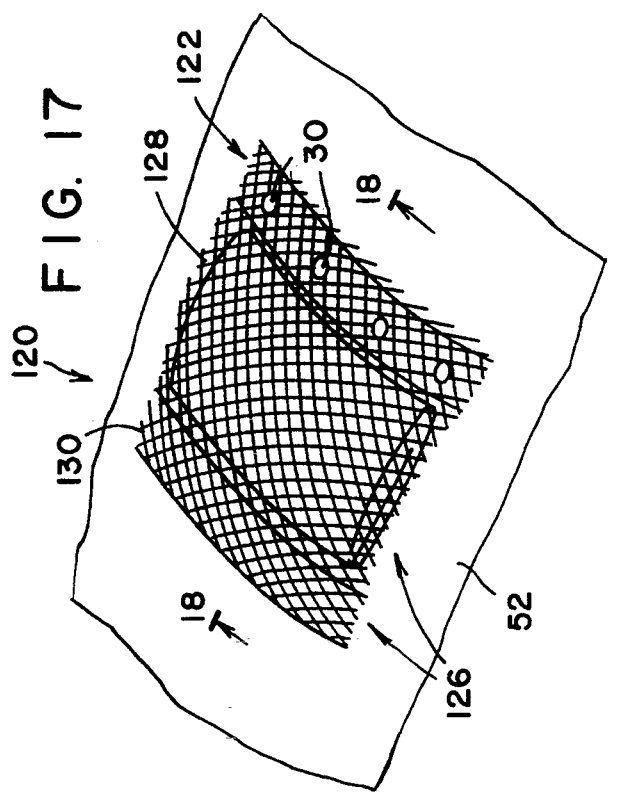
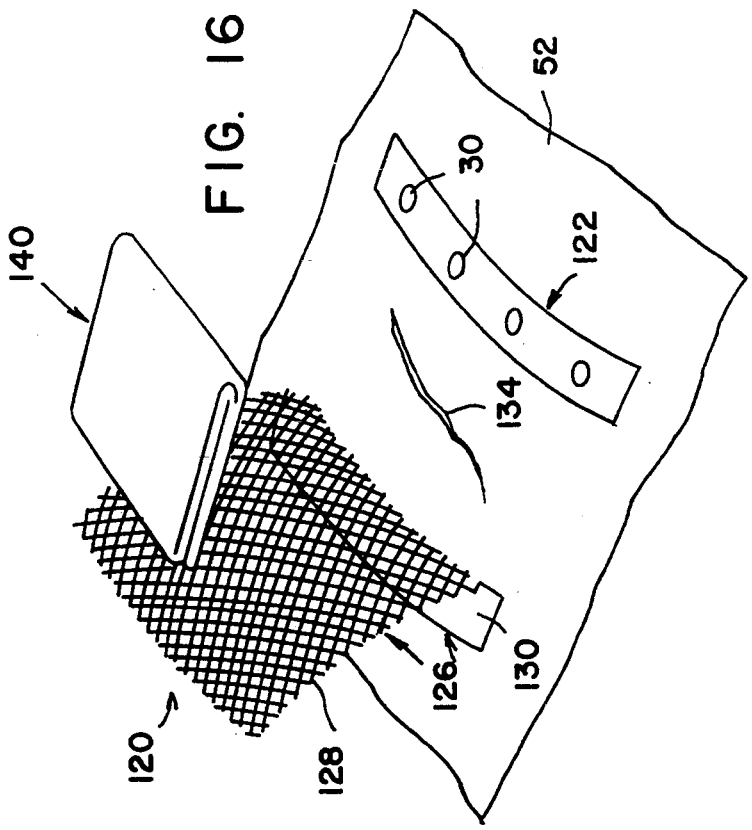

WOUND DRESSING SECUREMENT SYSTEM

BACKGROUND OF THE INVENTION

This invention pertains to medical devices for the care of wounds, and more particularly to a wound dressing securement device that securely holds a dressing on a wound and permits easy removal and interchange of the wound dressing.

A wound is generally manifested by a breach in the skin that may be due to injury or surgery. The healing process is normally promoted by treating the wound with an antiseptic and dressing the wound with a suitable bandage. The wound dressing is usually secured by applying a self-securing attachment member such as adhesive tape directly over the dressing.

As healing progresses it is often beneficial to periodically change the wound dressing. Thus the adhesive tape that secures the wound dressing must be removed, generally by peeling the tape from the skin in the area of the wound. In many instances, the peeling of adhesive tape from the area of the wound can irritate or aggravate a condition of soreness that is a common characteristic of a wound.

In order to minimize any discomfort and irritation that may accompany the change or removal of a wound dressing, it is well known to utilize wound dressing securement devices that do not require adhesive attachment of the dressing. One known wound dressing securement device includes a pair of remotely positioned adhesive strips with releasable ties or laces such as the Dermicel® Montgomery strap made by Johnson & Johnson. The adhesive strips are secured to the skin at a predetermined distance from opposite sides of a wound and have a marginal non-adhesive perforated portion for the lacing.

The wound dressing or bandage for the wound is held in place between the spaced adhesive strips by tying together the lacing that extends from each adhesive strip such that the tied lacing secures the wound dressing on the wound.

U.S. Pat. No. 4,423,731 shows a similar construction of two spaced adhesive strips with lacing bonded to the strips. The wound dressing is held in position on the wound beneath the tied lacing rather than being held in place by adhesive securement.

When the wound dressing is to be changed, the lacing is untied. The wound dressing can then be accessed and changed without the need to remove the oppositely disposed, remotely positioned adhesive strips or the untied lacing since they do not interfere with the changing of the wound dressing.

Thus the adhesive strips and lacing can be used again and again to secure each of the new replacement wound dressings. The prospect of wound irritation due to removal of self-securing adhesive attachment members such as adhesive tape, is thus eliminated since there is no need to undo an adhesive tape each time a wound dressing is changed.

As an alternative to using a Montgomery strap with lacing to secure the underlying wound dressing, it has been suggested by Johnson & Johnson that safety pins be inserted in the marginal perforations of each oppositely disposed adhesive strip. Opposing pairs of safety pins are hooked together by a rubber band to hold the underlying wound dressing in place. The wound dressing is accessed for replacement by opening the safety pins inserted in one of the adhesive strips to release the respective rubber bands.

Whether a wound dressing is secured by lacing or rubber bands, there must be separate manipulation of laces, rubber bands and safety pins each time a wound dressing is secured or accessed for replacement.

The manipulation of individual laces, safety pins and rubber bands whenever a wound dressing is changed is a time consuming procedure that can be discomforting to the patient and tedious to the caregiver. Occasionally a lacing must be retied or adjusted and a rubber band must be changed from one size to another before a desirable securement of the wound dressing is accomplished. Thus a supply of different sized rubber bands must be stocked.

Another wound dressing securement device which requires manipulation of individual connectors as shown in U.S. Pat. No. 363,538, includes a pair of adhesive strips, each having one hook or stud joined by a rubber band. Use of several pairs of the disclosed device is suggested for large wounds. This device thus requires tedious manipulation of adhesive strips and individual rubber bands.

U.S. Pat. No. 1,774,489 shows plaster strips for placement at opposite sides of a wound. Each strip includes an elongated metal bar formed with spaced hooks. The hooks of the opposing strips are laced together with a string. The metal bar in this device may be difficult to conform to curved portions of the anatomy, thus limiting the use of the device.

U.S. Pat. No. 2,196,296 shows three adhesive strips, two of which include a row of parallel threads. The third strip is used as a tensioning device for the threads to hold the wound dressing. This device is unduly complicated and requires detachment of one of the adhesive strips to change a wound dressing.

U.S. Pat. No. 4,723,146 shows a frame-like adhesive member that employs releasable straps having Velcro® securements to hold a wound dressing. The Velcro® securements are in the form of small patches to avoid entanglement with the wound dressing and do not permit a wide range of adjustability.

It is thus desirable to provide a wound dressing support system that is simple and easy to manipulate, provides a wide range of adjustability and does not require separate tying and untying of individual securement points.

OBJECTS AND SUMMARY OF THE INVENTION

Among the several objects of the invention may be noted the provision of a novel wound dressing securement device, a novel wound dressing securement device having an 10 adhesive base member with a plurality of sheet retention members engagable with a hold-down sheet member, a novel wound dressing securement device with a hold-down sheet member having a plurality of connection points defined by openings in the sheet, a novel wound dressing securement device with a stretchable hold-down sheet member to hold an underlying wound dressing in place, a novel wound dressing securement device having a hold-down sheet joined to an adhesive base member, a novel wound dressing securement device having a hold-down sheet member that can be quickly and easily installed and removed from the site of a wound to provide easy access to and securement of a wound dressing, a novel wound dressing securement device that eliminates the need for laces, safety pins, rubber bands and straps, and a novel method for securing a wound dressing to a wound.

Other objects and features of the invention will be in part apparent and in part pointed out hereinafter.

In accordance with the invention, the wound dressing securement device in one embodiment includes a pair of flexible adhesive base member strips adapted to be secured to the skin at opposite sides of a wound with sufficient spacing to accommodate a wound dressing between the base members. A plurality of sheet retention members project vertically from an exposed surface of each of the base members. The sheet retention members, which include a sheet engagement head, are arranged in a predetermined pattern on the base member.

After a wound dressing is applied on the wound, a hold-down sheet member having a plurality of engagement openings is joined to the base members to straddle the space between the base members and cover and hold the wound dressing on the wound. The sheet is thus engaged with the sheet retention members that extend vertically from the base member. Respective openings in the hold-down sheet member receive the engagement heads of respective sheet retention members to provide a slip-resistant connection.

The hold-down sheet member is preferably formed of a stretchable material such as a plastic mesh or plastic netting. The stretchability of the hold-down sheet member facilitates alignment and engagement of the openings in the sheet member with the sheet retention members, and also permits development of a slight tension in the hold-down sheet member to hold the underlying wound dressing in place.

Since the hold-down sheet member is formed as a unit, it can be handled as a unit to accomplish the engagement with a plurality of sheet retention members. Thus there is no need to manipulate a plurality of independent individual connection devices such as laces, rubber bands or safety pins.

When a wound dressing is to be accessed for removal or replacement, the hold-down sheet is disengaged as a unit from the sheet retention members on at least one of the base members. Disengagement is accomplished by simply pulling the hold-down sheet in a substantially vertical direction away from the sheet retention members. The wound dressing can then be separated from the wound.

After a new wound dressing is applied to the wound, the same hold-down sheet member can be reused. The base members can remain in place at opposite sides of the wound for substantially the entire healing cycle.

Since engagement and disengagement of the hold-down sheet member is accomplished quickly and easily, there is little, if any, discomfort to the patient during changing of the wound dressing.

In another embodiment of the invention, a single annular base member is provided to surround the wound and includes sheet retention members in circular array on the base member. In still another embodiment of the invention, the hold-down sheet member is bonded to one adhesive base member and detachably engagable to another adhesive base member.

The invention accordingly comprises the constructions and method hereinafter described, the scope of the invention being indicated in the claims.

DESCRIPTION OF THE DRAWINGS

In the accompanying drawings,

FIG. 1 is a simplified schematic perspective view of a wound dressing securement device incorporating one embodiment of the invention;

FIG. 2 is an enlarged fragmentary sectional view thereof, taken on the line 2—2 of FIG. 1;

FIG. 3 is an enlarged fragmentary plan view thereof;

FIG. 4 is a simplified schematic plan view of the base member and sheet retention members thereof;

FIG. 5 is an elevational view of the FIG. 4 structure;

FIG. 6 is an enlarged sectional view taken on the line 6—6 of FIG. 5;

FIG. 10 is a simplified plan view of another embodiment of the invention;

FIG. 11 is a side elevational view thereof;

FIG. 12 is an enlarged fragmentary sectional view thereof including the hold-down sheet member;

FIGS. 13 and 14 are simplified schematic perspective views showing sequential assembly of another embodiment of the wound dressing securement device;

FIG. 15 is an enlarged sectional view thereof, taken on the line 15—15 of FIG. 14;

FIGS. 16 and 17 are simplified schematic perspective views showing sequential assembly of a further embodiment of the wound dressing securement device; and, FIG. 18 is an enlarged sectional view thereof, taken on the line 18—18 of FIG. 17.

Corresponding reference characters indicate corresponding parts throughout the several views of the drawings.

DETAILED DESCRIPTION OF THE INVENTION

Figure 7:
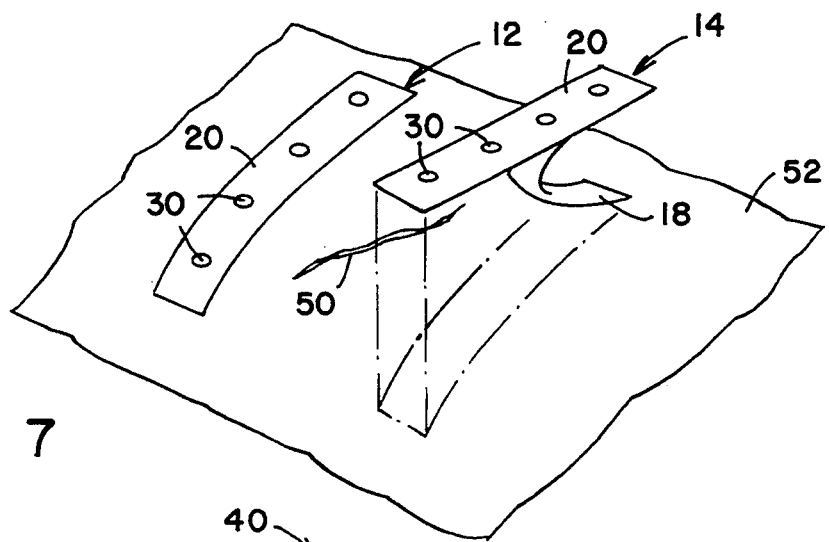
FIGS. 7-9 are simplified schematic perspective views showing a sequential positioning and assembly of the wound dressing securement device.

Referring to the drawings, a wound dressing securement device incorporating one embodiment of the invention is generally indicated by the reference number 10 in FIG. 1.

The securement device 10 includes a pair of flexible base members 12 and 14 having an adhesive attachment surface 16 covered with a silicone release paper 18 (FIGS. 6 and 7) prior to use. The base members 12 and 14, which are identical, are in the form of strips of a suitable biocompatible adhesive material, preferably a hydrocolloid such as Stomahesive ® sold by the ConvaTec Division of Bristol-Myers Squibb.

A non-adhesive surface 20 is provided on an obverse side of the base members 12 and 14 preferably by applying a layer of plastic such as polyethylene to the base members 12 and 14.

A plurality of sheet retention members 30 are joined to the base members 12 and 14 in a predetermined pattern such as a spaced row, and project in a vertical direction from the non-adhesive surface 20. The sheet retention members 30 are formed of a suitable plastic such as polyethylene and are ultrasonically welded to the non-adhesive plastic surface 20.

A typical sheet retention member 30 (FIGS. 4 and 5) includes a stem portion 32 with an enlarged generally circular base end 34 that contacts the surface 20 of the base member 12 and an oppositely disposed engagement head 36 also of generally circular shape.

The securement device 10 further includes a flexible, stretchable hold-down sheet member 40 preferably made of approximately 75% plastic such as ethylene vinyl acetate and approximately 25% rubber such as the type sold under the trademark Nordell ® rubber. The sheet member 40 is in the form of a mesh or netting having a grid-like pattern of openings 42 that are preferably diamond shaped as defined by ribs or webbing 44. The ribs or webbing 44 do not slide relative to each other but are integrally joined at their intersections. The sheet member 40 can be supplied in roll form or in sheets of predetermined size. In either case, the sheet stock can be easily trimmed to a desired size with a pair of scissors or prepackaged in a wrapping before use.

In using the securement device 10, the base members 12 and 14 are positioned on the skin 52 at opposite sides of a wound 50, a predetermined distance from the wound. Such positioning is accomplished by removing the release paper 18 from the adhesive surface 16 and attaching the base members 12 and 14 against the skin 52 in the desired position relative to the wound 50. The spacing between the base members 12 and 14 should be large enough to accommodate a suitable wound dressing 60.

Once the wound dressing 60 is placed on the wound 50, the hold-down sheet member 40 is engaged with the sheet retention members 30. The hold-down sheet is preferably sized to encompass the periphery of wound dressing 60 and a corresponding extent of the base members 12 and 14.

Engagement of the hold-down sheet member 40 is accomplished for example, with one base member at a time. Thus the sheet member 40 is pressed onto the engagement heads 36 of the sheet retention members 30 on one of the base members 12 or 14 to thread respective engagement heads 36 through corresponding aligned openings 42 in the sheet member 40. Alignment between the sheet retention members 30 and the openings 42 in the sheet member 40 can be facilitated by slightly stretching or folding the sheet member 40 onto the sheet retention members 30. Once the sheet member 40 is engaged with the sheet retention members 30, the webbing 44 is captured at the stem portion 32 between the base end 34 and the engagement head 36.

When the sheet member 40 is engaged with the base member 12, it can then be secured to the sheet retention members 30 of the base member 14 in a similar manner.

The stretchability of the sheet member 40 enables it to be placed under a slight tension while engaged with the base members 12 and 14 to hold the underlying wound dressing 60 in place on the wound 50.

Access to the wound dressing 60 for replacement of the dressing is easily accomplished by removing the sheet member 40 from one or both of the base members 12 and 14. Removal may require a slight stretching of the openings 44 in the sheet member 40 past the engagement heads 36 of the sheet retention members 30. The removed sheet member 40 can be reused if desired or replaced with a new sheet member 40.

Whether the sheet member 40 is partially detached by removal from one of the base members 12 and 14 or fully detached from both of the base members 12 and 14, a clear access is provided to the wound dressing 60 to permit changing of the dressing without the need to detach the base members 12 and 14 from the skin 52. The base members 12 and 14 can thus remain in their installed position on the skin 52 during the entire healing process which may involve several changes of the wound dressing 60.

Since the sheet member 40 is manipulated as a unit, it can be easily attached to a series of sheet retention members. 30 substantially simultaneously. As there are no separate independent individual components to manipulate, the installation of the sheet member 40 onto the base members 12 and 14 is relatively simple, quick and convenient.

The size of the securement device 10 can vary based on the intended location of the device and the size of the wound being dressed. A sample size specification for the device 10 includes base members 12 and 14 that measure approximately 3" wide by approximately 10½" long, and approximately 0.020 to 0.040" thick. The sheet retention members 30 have an overall height of approximately 3/16" with the engagement head 36 approximately 5/16" in diameter and approximately 1/16" thick. The stem portion 32 is generally circular and approximately 7/64" in diameter. The base end 34 is approximately ¾" in diameter and approximately 1/32" thick. The sheet retention members 30 can be spaced approximately 1¾" apart.

The sheet member 40 is approximately 0.035" thick with the diamond shaped openings 42 measuring approximately 5/16" from intersection to intersection of the webbing 44.

Another embodiment of the wound dressing securement device is generally indicated by the reference number 70 in FIG. 12.

The securement device 70 includes a base member 72 similar to the base member 12. A plurality of sheet retention members 74 are joined to the base member 72 in a manner similar to that previously described for securing the sheet retention members 30 to the base members 12 and 14.

The sheet retention members 74 include an elliptically shaped base end 82 and a generally rectangular engagement head 84 connected by a stem portion 86 similar to the stem portion 32 of the sheet retention member 30.

The securement device 70 further includes a hold-down sheet member 90 (FIG. 12) similar to the hold-down sheet member 40.

The securement device 70 is used in a manner similar to that previously described for the securement device 10, with two of the base members 72 being used at opposite sides of a wound and engaged with the sheet member 90 via the sheet retention members 74.

The sample size specification for the device 70 is generally similar to that of the device 10, except for the sheet retention member 74. The overall height of the sheet retention member 74 is approximately 9/64". The engagement head 84 is approximately 5/16" long, 3/16" wide and 1/16" thick. The base end 82 is approximately ¾" long, 13/32" wide and 1/32" thick. The stem portion 86 is generally rectangular with side dimensions of approximately 0.100 to 0.190". Preferably the sheet retention members 74 are positioned on the base member 72 such that the longer length of the engagement head 84 is parallel to the elongated length of the base member 72.

Another embodiment of the wound dressing securement device is generally indicated by the reference number 100 in FIGS. 13-15.

The securement device 100 includes a flexible annular base member 102 having the same constituents as the base member 12. The base member 102 is thus formed of a hydrocolloid such as made under the trademark Stomahesive ® and has an adhesive attachment surface 104. The base member 102 also includes an annular layer 106 of plastic such as polyethylene which receives a circular array of the sheet retention members 30 joined to the base member 102 in a manner similar to that previously described for securing the sheet retention members 30 the base members 12 and 14. The sheet retention members 30 are spaced at predetermined angular intervals.

Figure 8:
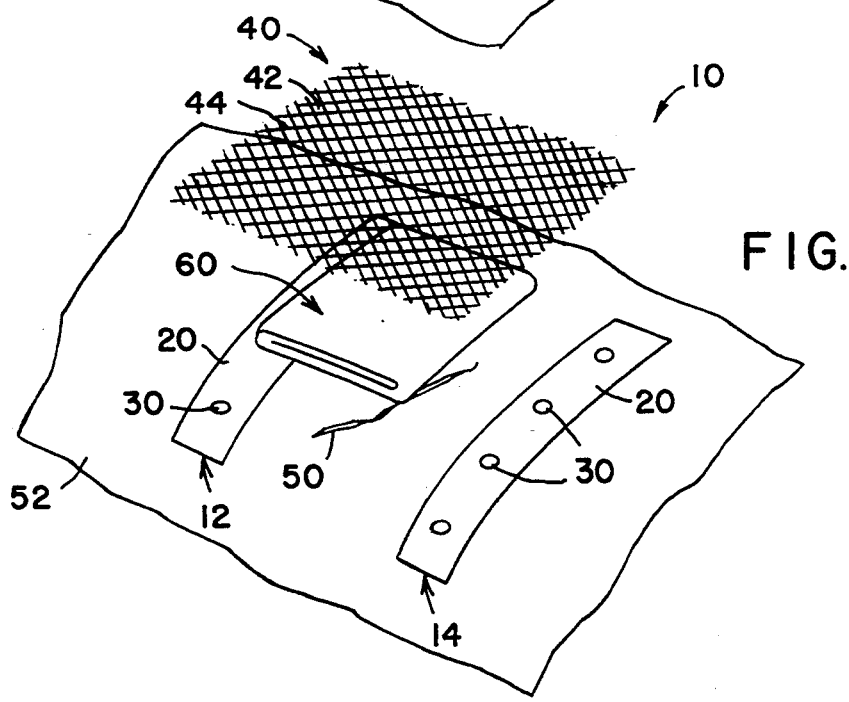
Figure 9:
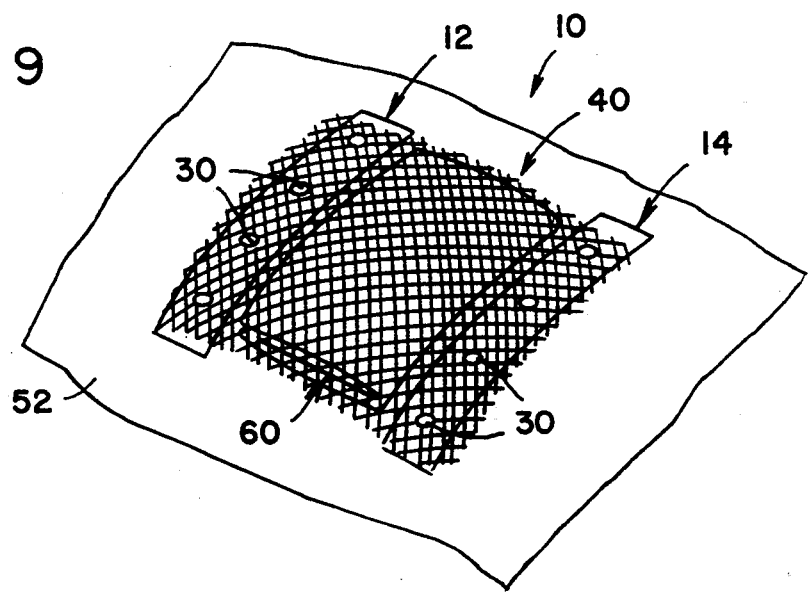

The securement device 100 further includes a hold-down sheet member 110 similar to the hold-down sheet member 40. As shown, the hold-down sheet member 110 can include a circular periphery or the generally rectangular periphery of FIGS. 8 and 9, provided the hold-down sheet fully encompasses the sheet retention members 30.

The securement device 100 is used in a manner similar to that previously described for the securement device 10 with the base member 102 spaced from and surrounding a wound 112. The base member 102 is engaged with the sheet member 110 via the sheet retention members 30 to hold an underlying wound dressing 114 in place on the wound 112.

A further embodiment of the wound dressing securement device is generally indicated by the reference number 120 in FIGS. 16–18.

The securement device 120 includes a base member 122 similar to the base member 12, and a combination member 126. A plurality of sheet retention members 30 are joined to the base member 122 in a manner similar to that previously described for securing the sheet retention members 30 to the base member 12.

The combination member 126 includes a hold-down sheet member 128 joined to a base member strip 130. The hold-down sheet member 128 is similar to the sheet member 40 and the base member strip 130, which includes a plastic layer 132, is similar to the base member 14.

The hold-down sheet 128 can be joined to the base member 14 by ultrasonic welding to the plastic layer 132 or adhesive bonding to the base member strip 130 in any suitable known manner. Since the hold-down sheet 128 is welded or bonded to the base member 130, there is no need to provide for sheet retention members on the base member 130.

The combination member 126 can be stocked in rolls and trimmed to size as needed or supplied in pre-cut sizes that can also be trimmed if necessary.

In using the securement device 120, the base members 122 and 126 are positioned on the skin 52 at opposite sides of a wound 134. The base members 122 and 126 are secured to the skin 52 a predetermined distance from the wound 134 after removing the release paper (not shown) from the adhesive attachment surfaces 136 and 138 (FIG. 18) of the base members 122 and 126.

The hold-down sheet 128 of the combination member 126 is then extended across a wound dressing 140 that has been applied to the wound 134. The hold-down sheet 128 is engaged with the sheet retention members 30 on the base member 122 to hold the underlying wound dressing 140 in place on the wound 134.

Access to the wound dressing 140 for replacement of the dressing is accomplished by disengaging the sheet member 128 from the retention members 30 of the base member 122. A replacement wound dressing (not shown) is held in place by reengaging the sheet member 128 with the retention members 30 of the base member 122.

Some advantages of the invention evident from the foregoing description include a wound dressing securement device with a one-piece sheet member that is commonly joined to a series of sheet retention members provided on one or more base members. Thus only one sheet member need be manipulated for connection to the base member(s). The connection or engagement between the sheet member and the base member(s) is quickly and easily accomplished.

The stretchability and foldability of the sheet member makes it easy to align the engagement openings in the sheet member with the sheet retention members and permits establishment of a desirable tension on the sheet member. Because the sheet member is a one-piece unit, it can provide a substantially uniform gentle holding pressure on the wound dressing for enhanced comfort of the patient.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A wound dressing securement device comprising,
   (a) two flexible base members, each having an adhesive attachment surface and a non-adhesive obverse surface, said base members being adapted to be spaced from each other on opposite sides of a wound,
   (b) a plurality of sheet retention members joined to each of said base members in a predetermined pattern and projecting from the obverse surface of said respective base member, and
   (c) a flexible hold-down sheet member of stretchable material for superposition over a wound dressing, said sheet member having a pattern of openings for receiving respective ones of said sheet retention members for stretchable engagement of said sheet retention members by said sheet member.

2. The wound dressing securement device as claimed in claim 1 wherein said openings are of diamond shape.

3. The wound dressing securement device as claimed in claim 1 wherein said sheet member includes openings in the shape of diamonds, said openings forming a grid-like pattern in said sheet member.

4. The wound dressing securement device as claimed in claim 1 wherein said sheet member is in the form of an elastic mesh.

5. The wound dressing securement device as claimed in claim 1 wherein said sheet member is in the form of an elastic netting.

6. The wound dressing securement device as claimed in claim 1 wherein the non-adhesive obverse surface of said base member is formed with plastic material.

7. The wound dressing securement device as claimed in claim 6 wherein said sheet retention members are formed of plastic and are ultrasonically welded to the non-adhesive surface of said base member.

8. The wound dressing securement device as claimed in claim 1 wherein said sheet retention members include a stem portion having an engagement head that is receivable in the engagement means of said sheet member.

9. The wound dressing securement device as claimed in claim 8 wherein said sheet member includes openings and the engagement heads of said stem portions are receivable in respective ones of said openings of said sheet member such that reception of the engagement heads in the respective openings of said sheet member normally prevent disengagement of the sheet member from said sheet retention members.

10. The wound dressing securement device as claimed in claim 9 wherein said sheet member is in the form of a stretchable elastic netting having said openings.

11. The wound dressing securement device as claimed in claim 10 wherein said openings have a smaller dimension than said engagement head and said sheet member is stretchable to engage respective said openings with respective said engagement heads.

12. The wound dressing securement device as claimed in claim 1 wherein said sheet retention members are rigid and project vertically from said base member.

13. The wound dressing securement device as claimed in claim 1 wherein said adhesive is a hydrocolloid adhesive.

14. A wound dressing securement device comprising,
 (a) a flexible base member having an adhesive attachment surface and a non-adhesive obverse surface, said base member being adapted to at least partly circumscribe a wound,
 (b) a plurality of sheet retention members joined to the base member in a predetermined pattern and projecting from the obverse surface of said base member, and
 (c) a flexible hold-down sheet member of stretchable material for superposition over a wound dressing, said sheet member having a pattern of openings for receiving respective ones of said sheet retention members for stretchable engagement of said sheet retention members by said sheet member.

15. The wound dressing securement device as claimed in claim 14 wherein said base member is in the form of an elongated strip.

16. The wound dressing securement device as claimed in claim 14 wherein said base member is of annular form.

17. A wound dressing securement device comprising,
 (a) two flexible base members, each base member having an adhesive attachment surface and a non-adhesive obverse surface, said base members being adapted to be spaced from each other on opposite sides of a wound,
 (b) a plurality of sheet retention members joined to said first base member in a predetermined pattern and projecting from the obverse surface of said first base member, and
 (c) a flexible hold-down sheet member of stretchable material for superposition over a wound dressing, said sheet member being attached to said second base member, said sheet member having a pattern of openings for receiving respective ones of said sheet retention members and for stretchable engagement of said sheet retention members by said sheet member.

18. A method of securing a wound dressing to a wound comprising,
 forming two flexible strip members having an adhesive attachment surface and a non-adhesive obverse surface with projections extending therefrom,
 adhesively securing the attachment surface of the flexible strip members to the skin on opposite sides of a wound,
 placing a wound dressing on the wound,
 covering the wound dressing with an elastic hold-down sheet having a pattern of openings, and
 securing the elastic hold-down sheet to the two strip members at a plurality of locations by extending at least some of the projections through said openings and stretchably engaging said projections with said elastic sheet member.

19. A method of securing a wound dressing to a wound comprising,
 forming a flexible base member having an adhesive attachment surface and a non-adhesive obverse surface with projections extending from said obverse surface with projections extending from said obverse surface,
 adhesively securing the attachment surface of the flexible base member to the skin so as to extend at least partly around a wound,
 placing a wound dressing on the wound,
 covering the wound dressing with an elastic hold-down sheet having a pattern of openings, and
 securing the elastic hold-down sheet to the base member at a plurality of locations by extending at least some of said projections through said openings and stretchably engaging said retention members with said elastic sheet.

* * * * *